United States Patent

Shieh et al.

[11] Patent Number: 5,429,799
[45] Date of Patent: Jul. 4, 1995

[54] MICROWAVE DECOMPOSITION MACHINE

[75] Inventors: Yuh-Ren Shieh; Chi-non Chen; Jey-cherng Chen; Chun-yuh Yu, all of Hsinchu, Taiwan

[73] Assignee: Industrial Technology Research Institute, Hsinchu, Taiwan

[21] Appl. No.: 239,291

[22] Filed: May 6, 1994

[51] Int. Cl.⁶ .............................. A61L 2/12
[52] U.S. Cl. .................... 422/21; 422/309; 422/307; 241/606; 219/741
[58] Field of Search ........... 422/224, 225, 228, 21, 422/269–270, 307, 209, 309; 241/606; 219/739, 741, 752, 762

[56] References Cited

U.S. PATENT DOCUMENTS

| | | | |
|---|---|---|---|
| 4,563,335 | 1/1986 | Akiyama et al. | 422/159 |
| 4,599,216 | 7/1986 | Rohrer et al. | 422/21 |
| 4,975,246 | 12/1990 | Charm | 422/21 |
| 5,003,143 | 3/1991 | Marks et al. | 219/10.55 |
| 5,124,125 | 6/1992 | Brent | 422/21 |
| 5,191,184 | 3/1993 | Shin | 219/10.55 |
| 5,196,069 | 3/1993 | Cullingford et al. | 127/37 |
| 5,209,902 | 11/1993 | Matthews et al. | 422/21 |
| 5,213,758 | 5/1993 | Kawashima et al. | 422/21 |
| 5,223,231 | 6/1993 | Drake | 422/297 |
| 5,237,938 | 8/1993 | Fujimori et al. | 110/240 |

*Primary Examiner*—Robert J. Warden
*Assistant Examiner*—Theresa T. Snider
*Attorney, Agent, or Firm*—George O. Saile

[57] ABSTRACT

This invention describes a microwave decomposition machine and method to decompose and sterilize medical waste material using high energy density microwaves, 60 Kilowatts or greater. The medical waste is well stirred and there is no damage of the cavity due to arcing during the process. The decomposition process takes place in a sealed oxygen free atmosphere of 1.0% or less oxygen thereby preventing the discharge of any medical waste gases into the atmosphere. The microwave decomposition machine can be mounted on a vehicle for easy transport to the source of the medical waste material.

13 Claims, 2 Drawing Sheets

MICROWAVE DECOMPOSITION MACHINE

BACKGROUND OF THE INVENTION (1) Field of the Invention

The invention relates to the decomposition and sterilization of medical waste material and more particularly to the treatment of medical waste material with microwave energy in an inert atmosphere prior to disposal.

(2) Description of the Related Art

The disposing of medical waste material is a serious problem which is getting more and more serious as time goes on. Medical waste material must be properly treated before being disposed of in order to insure that soil or water supplies around dumping grounds or land-fill areas will not become contaminated with dangerous organisms. Incineration of medical waste material, which has long been an important method of treating medical waste, must be carried out with great care to prevent discharge of dangerous waste material into the atmosphere. Along with need for methods which will handle medical waste material safely is the need to handle such material economically.

A number of methods for dealing with medical waste material have been patented. A number of these patents describe the use of microwave energy to heat the waste material often in conjunction with other types of processing, for example Robert C. Drake in U.S. Pat. No. 5,223,231 or Norihiro Kawashima et al in U.S. Pat. No. 5,213,758. Minoru Fujimori et al in U.S. Pat. No. 5,237,938 describe an incinerator with a main burner into which a mixture of oil and water are injected to incinerate the medical waste material.

During the decomposition and sterilization of the medical waste material care must be taken to avoid discharging dangerous gases into the atmosphere. If microwave energy is used to heat medical waste material care must be taken to avoid waste material causing arcing in the vicinity of the rotary tank.

SUMMARY OF THE INVENTION it is a principle object of this invention to provide a machine which will safely decompose and sterilize medical waste material so that the decomposed and sterilized residue can be disposed of by conventional means.

It is a further object of this invention to provide a method which will safely decompose and sterilize medical waste material so that the decomposed and sterilized residue can be disposed of by conventional means.

It is a further object of this invention to provide a means to decompose, sterilize, and dispose of medical waste material economically and in a manner that will not expel dangerous material into either the atmosphere, ground or water supply.

These objectives are achieved by means of a machine which shreds medical waste material into strips of between about 10 to 20 cm in length with a width or diameter of less than about 2.5 cm and uses microwave energy in a sealed atmosphere to decompose and sterilize the medical waste material. The machine has a capability to provide a sealed atmosphere during the decomposition and sterilization process thereby preventing the discharge of any medical waste solids or gases into the atmosphere. The sealed atmosphere also makes it possible to prevent the leakage of oxygen from the outside atmosphere during the decomposition and sterilization process. The decomposed and sterilized medical waste gases are collected in a gas condenser attached to the machine. The solid decomposed and sterilized medical waste material can be discharged into a trolly to be removed for conventional disposal.

The sealed atmosphere is accomplished by means of an output door which forms a rotary joint between a fixed waveguide and a rotary tank. This output door forms a vacuum seal/and a microwave energy seal between the fixed waveguide and rotary tank. The output door also provides a means to discharge solid decomposed and sterilized medical waste material from the rotary tank.

First, an inert gas such as nitrogen or carbon dioxide is introduced into the tank to purge and expel the air inside the rotary tank. Then, the medical waste material is shredded and introduced into the rotary tank. A microwave generator generates microwave energy which is introduced into the rotary tank by means of a waveguide. Since the mixing blade is attached to the rotary tank containing the medical waste material particles there will not be arcing or other undesirable effects in the rotary tank. The microwave energy decomposes and sterilizes the medical waste material in the rotary tank. Gases generated during the decomposition and sterilization process are collected in a gas condenser. The microwave generator is then turned off, the output door between the rotary tank and the waveguide is opened and the solid decomposed and sterilized medical waste material is discharged from the rotary tank into a trolly for removal.

The machine can be mounted on a vehicle and transported to the source of the medical waste material such as a hospital, physician's office, dentist's office, etc.

DESCRIPTION OF THE PREFERRED EMBODIMENTS

Figure 1:
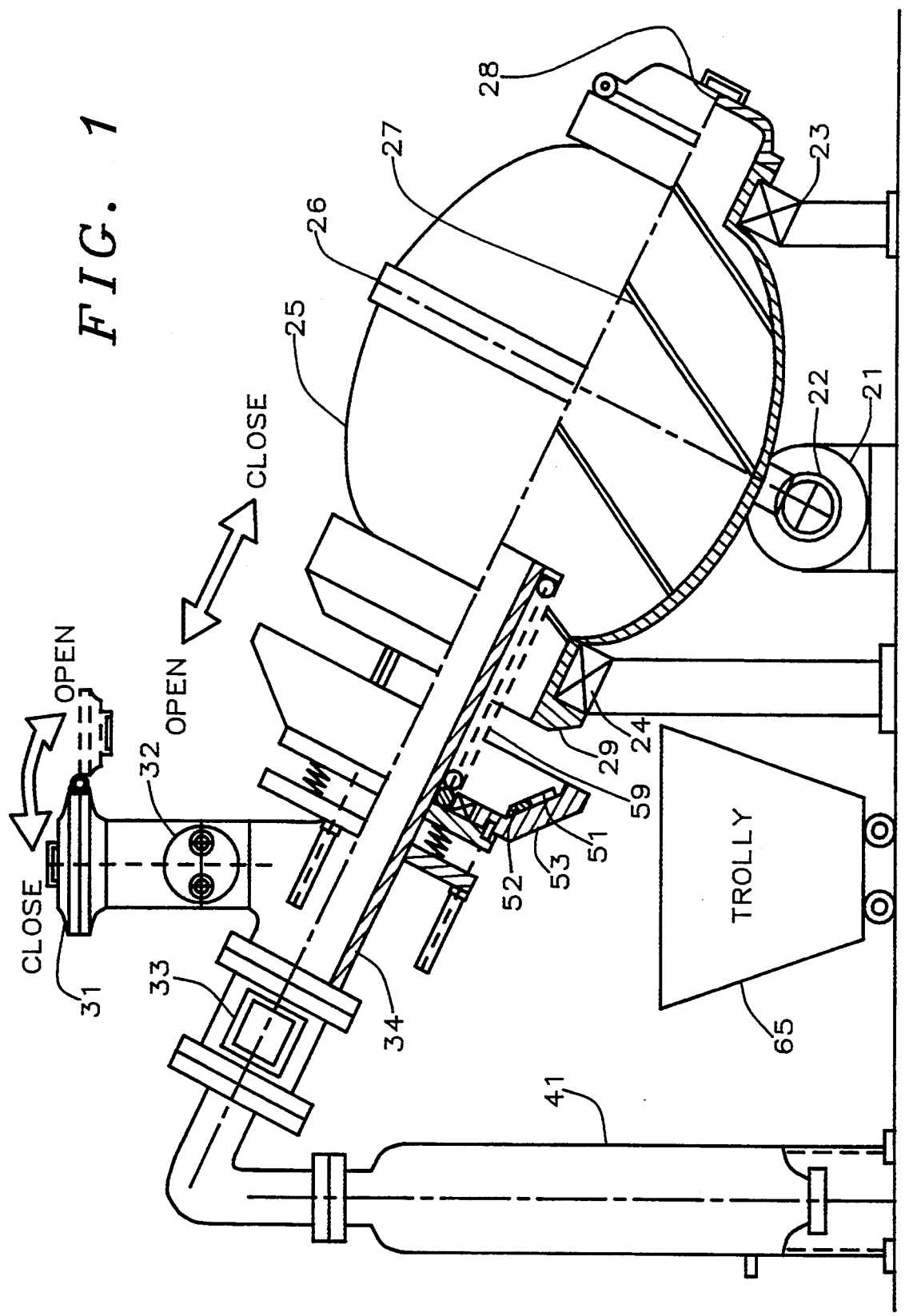
FIG. 1 is a cross sectional representation of the microwave decomposition machine.
Figure 2:
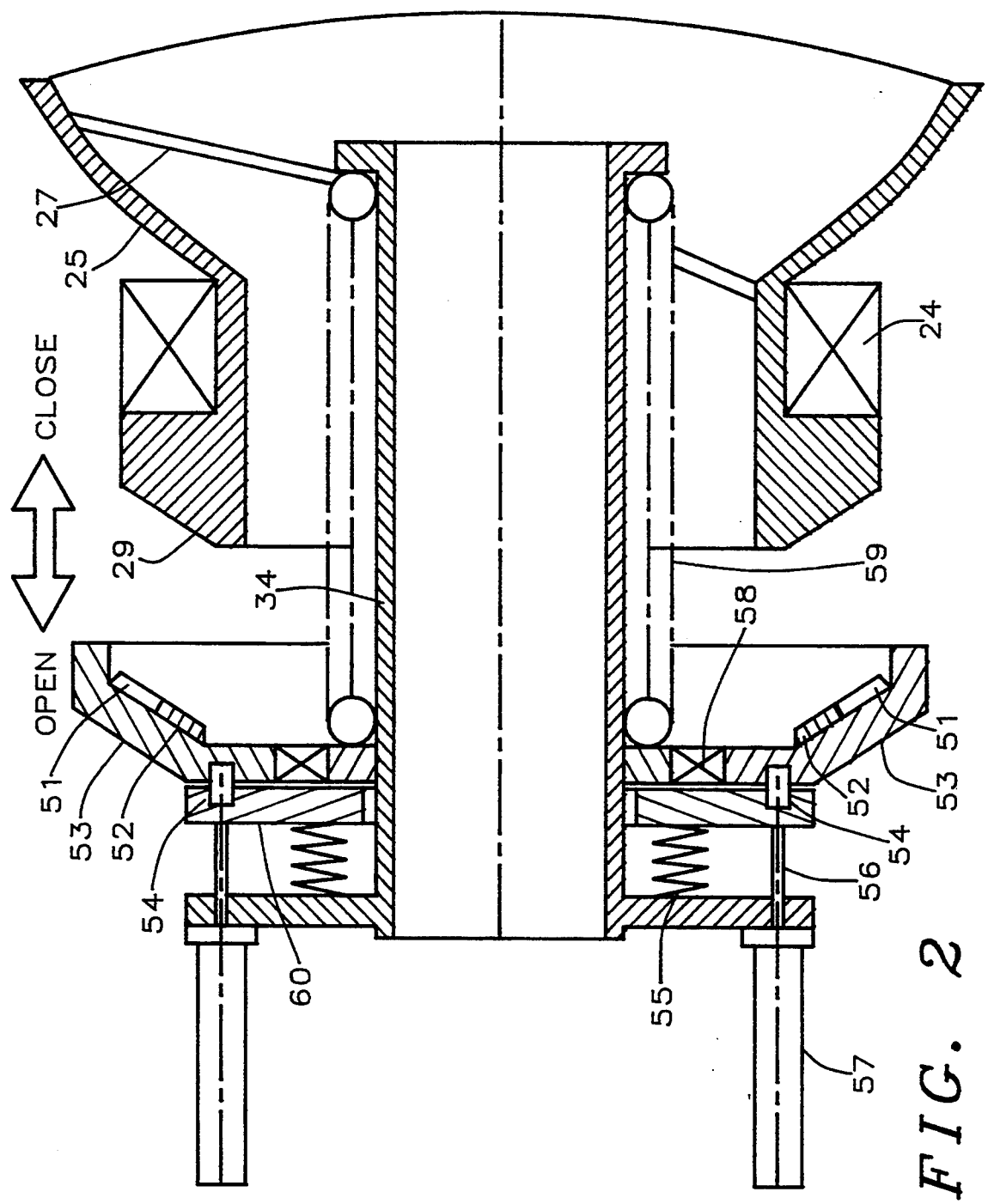
FIG. 2 is a cross sectional representation of the output door which serves as a rotary joint between the fixed waveguide and the rotary tank.

An embodiment of the microwave decomposition machine is shown in FIG. 1. The principle parts of the machine are an input door 31, shredder 32, a microwave generator 33, a waveguide 34, a rotary tank 25, a gas condenser 41, and an output door mechanism. Refer to FIG. 2 where the output door mechanism is shown. The principle parts of the output door mechanism are the end cover 53; the plunger plate 60; the rubber gasket 51, such as a sealing gasket; the metallic mesh gasket 52, such as a stainless steel or copper mesh gasket; the sliding bearing 54, such as a graphite sliding bearing; the rolling bearing 58; the metallic bellows 55; the plunger 56; the actuator 57; and the compression spring 59.

Refer now to FIGS. 1 and 2 for the embodiment of the method of decomposition and sterilization of medical waste material. At the beginning of the decomposition and sterilization cycle the output door is closed forming both a vacuum seal and a microwave energy seal between the fixed waveguide 34 and the rotary tank 25. Refer now more particularly to FIG. 2 which shows a cross sectional view of the output door. When the output door is closed the actuator 57 and the plunger 56 pushing on the plunger plate 60 force the end cover 53 in place against the sealing face 29 of the rotary tank 25 thereby compressing the compression spring 59. The rubber gasket 51 and the metallic mesh gasket 52 are compressed against the rotary tank sealing face 29 to form a gas tight seal and a microwave energy seal respectively. The rolling bearing 58 separates the end cover 53 from the fixed waveguide 34 and allows the end cover to rotate with respect to the fixed waveguide. Any gas which escapes through the rolling bearing 58 is prevented from escaping into the atmosphere by the metallic bellows 55 and by the graphite sliding bearing 54 between the end cover 53 and the plunger plate 60.

Refer now to FIG. 1 where is shown a cross sectional view of the microwave decomposition machine. At the beginning of the decomposition cycle the medical waste material to be treated is introduced through the input door 31. Then the input door 31 is closed and an inert gas such as nitrogen, carbon dioxide or the like (to keep oxygen less than about 1%) is introduced into the interior of the decomposition machine through a valve 28 at the end of the rotary tank 25 to purge the air inside. The output door is then closed as described above. The medical waste material is then shredded by the shredder 32 into strips of varying length, up to about 10 to 20 cm, with a width or diameter of less than about 2.5 cm. The shredded waste material then falls to the interior of the fixed waveguide 34 and from the fixed waveguide into the interior of the rotary tank 25 coming to rest against the helical mixing blades 27 attached to the inner surface of the rotary tank 25.

Next the microwave generator 33 generates microwave energy of about 60 Kilowatts which travels down the fixed waveguide 34 and into the interior of the rotary tank 25. The microwave generator may be chosen to be 915 MHz or 2450 MHz. The preferred frequency is 915 MHz because the generator is currently available and less expensive. The driving motor 21, worm gear 22 and gear ring 26 cause the rotary tank 25 to rotate while being supported by bearings 23, 24, and 58. The helical mixing blades 27 continually stir the shredded medical waste material particles which are decomposed and sterilized by the microwave energy.

The decomposition and sterilization process occurs in an oxygen free atmosphere inside the rotary tank 25. Any gases which are generated during the decomposition process are collected by the gas condenser 41 to be further recycled. The machine is completely sealed during the decomposition and sterilization process so no gaseous waste is discharged into the atmosphere. The gas condenser 41 may also be equipped with a disinfection device such as an ultraviolet light source.

Refer again to FIG. 2. At the completion of the decomposition cycle the microwave generator is turned off and the rotation of the rotary tank is reversed. The output door is opened by moving the end cover 53 away from the rotary tank 25.

Refer again to FIG. 1. With the rotation direction of the rotary tank 25 reversed; being driven by the driving motor 21, the worm gear 22, and the gear ring 26; the helical mixing blade 27 moves the decomposed and sterilized solid medical waste material out of the output door and into the trolley 65 for safe disposal. The microwave decomposition machine is then ready for the next batch of medical waste material.

Another embodiment of the invention consists of the microwave decomposition machine mounted on a truck or other suitable vehicle. The truck then transports the microwave decomposition machine to the source of the medical waste material such as a hospital, physician's office, dentist's office, etc. The microwave decomposition machine then processes the medical waste material as previously described and transports the microwave decomposition machine to the next source of medical waste material.

While the invention has been particularly shown and described with reference to the preferred embodiments thereof, it will be understood by those skilled in the art that various changes in form and details may be made without departing from the spirit and scope of the invention.

What is claimed is:

1. A machine using microwave energy in a sealed atmosphere to decompose and sterilize medical waste material, comprising:

a rotary tank with mixing blades attached to the inner surface of said rotary tank;

a microwave generator;

a fixed waveguide connecting said rotary tank to said microwave generator which transmits microwave energy from said microwave generator to the interior of said rotary tank;

an input door connected to said waveguide for introducing medical waste material into the machine;

an output door mechanism forming a rotary joint between said rotary tank and said fixed waveguide wherein said mechanism forms a vacuum seal, a microwave energy seal, and means for discharging solid decomposed and sterilized medical waste material;

means for collecting output gases of said decomposed and sterilized medical waste material connected to said microwave generator; and means for collecting solid said decomposed and sterilized medical waste material discharged from said output door mechanism.

2. The machine of claim 1 wherein there is mounted on said machine, means for shredding said medical waste material between said input door and said waveguide.

3. The machine of claim 2 wherein said shredding means is a shredder to shred said medical waste material into strips of varying lengths having a width or diameter of less than about 2.5 cm.

4. The machine of claim 1 wherein said mixing blades are heroical mixing blades.

5. The machine of claim 1 wherein said means for collecting said output gasses is a gas condenser.

6. The machine of claim 1 wherein said means for collecting said solid decomposed and sterilized medical waste material is a trolley comprised of a container mounted on wheels.

7. The machine of claim 1 wherein said rotary tank is rotated by means of a motor and gear attached to the exterior of said rotary tank.

8. A method of decomposing and sterilizing medical waste material, comprising:

providing a decomposing and sterilizing apparatus comprising a rotary tank with mixing blades attached to the inner surface of said rotary tank; a sealed atmosphere inside said rotary tank; a microwave generator; a fixed waveguide connecting said rotary tank to said microwave generator which transmits microwave energy from said microwave generator to the interior of said rotary tank; a mechanism forming a rotary joint between said rotary tank and said fixed waveguide wherein said mechanism forms a vacuum seal, a microwave energy seal, and a means to allow for discharging solid said decomposed and sterilized medical waste material; a means for collecting solid said decomposed and sterilized medical waste material; a means for collecting output gases of said decomposed and sterilized medical waste material; and an input door attached to a shredder;

placing medical waste material into said shredder by way of said input door;

shredding said medical waste material into strips of varying lengths having a width or diameter of less than about 2.5 cm;

allowing said shredded medical waste material to fall from said shredder to the inside said rotary tank;

generating microwave energy of 60 kilowatts with said microwave generator;

transmitting said microwave energy to the interior of said rotary tank by means of said waveguide;

decomposing and sterilizing said medical waste material by means of exposing said shredded medical waste material to said microwave energy in said sealed atmosphere;

collecting any output gasses produced during the decomposition and sterilization of said medical waste material; and collecting solid said decomposed and sterilized medical waste material.

9. The method of claim 8 wherein said sealed atmosphere consists essentially of nitrogen or carbon dioxide.

10. The method of claim 8 wherein said mixing blades attached to the inner surface of said rotary tank are helical mixing blades.

11. The method of claim 8 wherein said mixing blades attached to the inner surface of said rotary tank are used to expel said decomposed and sterilized solid medical waste material from said rotary tank.

12. The method of claim 8 wherein said means for collecting output gases is a gas condenser.

13. The method of claim 8 wherein said means for collecting solid said decomposed and sterilized medical waste material is a trolley comprised of a container mounted on wheels.

* * * * *